United States Patent
Park et al.

(10) Patent No.: US 8,815,277 B2
(45) Date of Patent: Aug. 26, 2014

(54) IN SITU FORMING HYDROGEL AND BIOMEDICAL USE THEREOF

(75) Inventors: Ki-Dong Park, Seoul (KR); Yoon-Ki Joung, Incheon (KR); Kyung-Min Park, Seoul (KR)

(73) Assignee: Ajou University Industry-Academic Cooperation Foundation, Suwon-si, Gyeonggi-do (KR)

( * ) Notice: Subject to any disclaimer, the term of this patent is extended or adjusted under 35 U.S.C. 154(b) by 0 days.

(21) Appl. No.: 13/381,843

(22) PCT Filed: Jul. 1, 2010

(86) PCT No.: PCT/KR2010/004292
§ 371 (c)(1),
(2), (4) Date: Dec. 30, 2011

(87) PCT Pub. No.: WO2011/002249
PCT Pub. Date: Jan. 6, 2011

(65) Prior Publication Data
US 2012/0100103 A1    Apr. 26, 2012

(30) Foreign Application Priority Data

Jul. 2, 2009 (KR) .................. 10-2009-0060370

(51) Int. Cl.
| A61F 2/00 | (2006.01) |
| A61K 45/00 | (2006.01) |
| A61K 39/395 | (2006.01) |
| A61K 39/00 | (2006.01) |
| C07K 14/495 | (2006.01) |
| C07K 14/50 | (2006.01) |
| C07K 14/485 | (2006.01) |
| A61L 27/54 | (2006.01) |
| A61K 9/00 | (2006.01) |
| A61L 27/52 | (2006.01) |
| A61K 47/42 | (2006.01) |

(52) U.S. Cl.
CPC .................. *A61L 27/52* (2013.01); *A61L 27/54* (2013.01); *A61L 2300/41* (2013.01); *A61K 9/0024* (2013.01); *A61L 2300/602* (2013.01); *A61L 2400/06* (2013.01); *A61L 2300/416* (2013.01); *A61L 2300/43* (2013.01); *A61L 2300/414* (2013.01); *A61L 2300/252* (2013.01); *A61L 2300/256* (2013.01); *A61K 47/42* (2013.01); *A61L 2300/406* (2013.01)
USPC .... 424/423; 424/85.1; 424/141.1; 424/184.1; 514/8.9; 514/9.1; 514/9.6

(58) Field of Classification Search
USPC ........ 424/85.2, 141.1, 184.1, 649, 85.5, 85.6, 424/85.7; 514/11.3, 11.4, 11.9, 17.2, 6.5, 514/7.7, 8.1, 8.2, 8.4, 8.8, 8.9, 9.1, 9.6
See application file for complete search history.

(56) References Cited

U.S. PATENT DOCUMENTS

| 5,232,984 A | 8/1993 | Hubbell et al. | |
| 2008/0069857 A1* | 3/2008 | Yeo et al. ....................... | 424/426 |
| 2009/0022683 A1 | 1/2009 | Song et al. | |

FOREIGN PATENT DOCUMENTS

| KR | 10-0266912 | 12/2000 |
| KR | 10-2007-0038738 | 4/2007 |
| KR | 10-2007-0076386 | 7/2007 |
| KR | 10-0776297 | 11/2007 |
| KR | 10-2009-0002946 | 1/2009 |
| WO | WO 00/09199 | 2/2000 |

OTHER PUBLICATIONS

Lee et al. ("An injectable enzymatically crosslinked hyaluronic acid-tyramine hydrogel system with independent tuning of mechanical strength and gelation rate," in Soft Matter, 2008, 4, 880-887).*
Leach et al. ("Characterization of protein release from photocrosslinkable hyaluronic acid-polyethylene glycol hydrogel tissue engineering scaffolds," in Biomaterials, 26 (2005) 125-135).*
Sakai et al. ("An injectable, in situ enzymatically gellable, gelatin derivative for drug delivery and tissue engineering," Biomaterials, No. 30, pp. 3371-3377 Apr. 5, 2009).*
Lee et al. ("An injectable hyaluronic acid-tyramine hydrogel system for protein delivery," in Journal of Controlled Release, No. 134, pp. 186-193, Dec. 7, 2008).*

Motoichi Kurisawa et al., "Injectable biodegradable hydrogels composed of hyaluronic acid-tyramine conjugates for drug . . . ", Chemical Communications, 2005, pp. 4312-4314.

Rong Jin et al., "Enzyme-mediated fast in situ formation of hydrogeles from dextran-tyramine conjugates", Biomaterials, 2007, pp. 2791-2800.

Li-Shan Wang et al., "The role of stiffness of gelatin-hydroxyphenylpenylpropionic acid hydrogels formed by enzyme-mediated . . . ", Biomaterials, 2010, pp. 8608-8616.

Shinji Sakai et al., "An injectable, in situ enzymatically gellable, gelatin derivative for drug delivery and tissue engineering", Biomaterials, 2009, pp. 3371-3377.

Shinji Sakai et al., "Synthesis and characterization of both ionically and enzymatically cross-linkable alginate", Acta Biomaterialia, 2007, pp. 495-501.

\* cited by examiner

*Primary Examiner* — Blessing M Fubara
(74) *Attorney, Agent, or Firm* — Revolution IP, PLLC

(57) ABSTRACT

Disclosed are in situ-forming injectable hydrogel and medical uses thereof. In the in situ-forming injectable hydrogel two or more homogeneous or heterogeneous polymers are bonded to each other by a dehydrogenation reaction between phenol or aniline moieties on adjacent polymers, wherein a polymer backbone is grafted with a phenol or aniline moiety using a linker. In contrast to conventional hydrogel, the in situ-forming injectable hydrogel is superior in terms of in vivo stability and mechanical strength thanks to the introduction of a water-soluble polymer as a linker which leads to an improvement in the reactivity of phenol or aniline moieties. Having the advantage of superior bio stability and mechanical strength, the hydrogel finds a variety of applications in the biomedical field.

4 Claims, 7 Drawing Sheets

Needle gage: 26"

experimental method experimental result degenerative lesion indicated with a needle hole forming in disc formed hole and damaged AF polymer injection GHPA hydrogels GPEG-TA hydrogels

IN SITU FORMING HYDROGEL AND BIOMEDICAL USE THEREOF

CROSS REFERENCE TO PRIOR APPLICATIONS

This application is a National Stage Patent Application of PCT International Patent Application No. PCT/KR2010/004292 (filed on Jul. 1, 2010) under 35 U.S.C. §371, which claims priority to Korean Patent Application No. 10-2009-0060370 (filed on Jul. 2, 2009), which are all hereby incorporated by reference in their entirety.

TECHNICAL FIELD

The present invention relates to an in situ-forming injectable hydrogel improved in biostability and mechanical strength and the biomedical use thereof.

BACKGROUND ART

Due to their high biocompatibility, high water content and excellent permeability to nutrients and metabolites, hydrogels have been extensively studied as biomaterials to be used in various biomedical applications, such as implants, drugs and cell delivery carriers. Hydrogels may be prepared from naturally occurring or synthetic polymers and be formed in a chemical and physical three-dimensional crosslinked network. Over the last decade, trends in hydrogel study have shifted to in situ-forming hydrogels, which are formed at the actual site following the in vivo injection of a polymer solution.

In situ forming hydrogels may be used in injectable hydrogel systems. Based on minimally invasive techniques, injectable hydrogel systems have attracted intensive attention because they make up easy formulations which are comfortable to patients. These systems may composed of injectable fluids which can form hydrogels in vivo, e.g., in tissues, organs, or coeloms before being solidified upon injection using minimally invasive methods.

For example, injectable hydrogel systems do not require surgical procedures for their implantation, but various drugs and bioactive molecules can be encapsulated easily into the hydrogel by simple mixing. It is possible to fill defected or depressed sites of the body cavities with injectable hydrogel. Injectable hydrogel systems have poor mechanical properties, but enjoy the advantages of exhibiting high cell seeding efficiency, being useful as carriers for bioactive drugs such as peptides, proteins and DNA, and effectively delivering nutrients to cells.

In-situ hydrogel formation may be the result of chemical crosslinking achieved by UV-polymerization or Michael addition or by physiochemical crosslinking such as ionic bonding, stereocomplex formation or thermosensitive binding following hydrophobic interaction. When formed by chemical crosslinking, the in-situ formed hydrogels are restricted in use due to their cytotoxicity and poor in vivo safety which results mainly from the use of toxic additives such as a photoinitiator or a crosslinking agent. In contrast, the in-situ forming hydrogels prepared by physiochemical crosslinking are in principle free of the toxic additives, but suffer from the disadvantages of low mechanical strength and stability.

It is particularly difficult in the case of photosensitive hydrogels to uniformly mix a solution of the precursor polymer solution with cells or drugs due to the high viscosity thereof, and these are also disadvantageous in that their preparation takes a long period of time. On the other hand, when the stereocomplexed hydrogel degrades, it produces acidic by-products which cause cytotoxicity and necrosis to the surrounding tissue.

In order to overcome these problems, an enzyme-triggered in-situ forming hydrogel has recently been developed. This crosslinked hydrogel results from the in situ polymerization of a polymer in the presence of horseradish peroxidase (HRP) and hydrogen peroxide ($H_2O_2$). In addition to having excellent in situ safety, the enzyme-triggered in-situ forming hydrogel enjoys the advantage of the chemically crosslinked hydrogel, that is, high mechanical strength.

The enzyme-triggered in-situ forming hydrogels developed so far are as follows: dextran-tyramine (dec-TA) (Rong Jin et al, Biomaterials 2007), hyaluronic acid-tyramine (HA-TA) (Motoichi Kurisawa et al, Chem. Commun. 2005), gelatin-hydroxypropionic acid (GHPA) (Lishan Wang et al, Biomaterials 2009), gelatin-tyramine(GTA) (Shinji Sakai et al, Biomateirals 2009), and alginic acid-hydroxyphenylacetic acid (AHPA) (Shinji Sakai et al, Acta Biomaterialia 2007).

Hydrogels which are formed in situ by enzyme-mediated crosslinking from hyaluronic acid-tyramine are commercially available from LifeCore and there have been many related PCT and U.S. patents issued. The HRP-mediated coupling reaction of phenol moieties in the polymer backbones occurs via a carbon-carbon bond at the ortho positions and/or via a carbon-oxygen bond between the carbon atom at the ortho position and the phenoxy oxygen.

The physiochemical properties of the formed hydrogel, such as gelation time, mechanical strength, biodegradability, etc., can be easily controlled with the concentration ratio of HRP to $H_2O_2$. However, these enzyme-triggered hydrogels suffer from the disadvantages of having poor stability and mechanical properties, attributable to the solubility of the polymer solution and the reactivity of phenol-phenol coupling.

For example, the amount of the polymer solutions in these hydrogels is restricted to the range of from as low as 1 to 5 wt % due to the high viscosity thereof. In practice, the high viscosity makes it difficult to uniformly mix cells or drugs within the hydrogels.

The low solubility of gelatin-tyramine (GTA) may lead to an opaque hydrogel and permit the polymer solution to be at a concentration of 5 wt % or less. Because the rate of solubility of gelatin is affected by other factors (especially low temperatures) there is a need to solve this problem.

As for gelatin-hydroxypropionic acid (GHPA) hydrogels, their mechanical strength is 600 Pa at best. This poor mechanical strength is attributed to the fact that the phenol moieties of the polymer backbone are directly bonded to each other. The mobility of the phenol moieties plays an important role in forming a phenol-phenol bond because the formation of radicals for phenol-phenol bonds requires that the distance between HRP molecules and phenol moieties be at least several angstroms (Å). Thus, drawbacks occur in structures where the phenol moieties are directly bonded.

Therefore, there is a need for an in situ forming hydrogel that is superior in terms of biostability and mechanical strength.

DISCLOSURE OF INVENTION

Technical Problem

Leading to the present invention, intensive and thorough research into in situ forming hydrogels, aiming to overcome the problems encountered in the art, resulted in the finding that the introduction of a hydrophilic polymer chain (water-soluble polymer) as a linker between a naturally occurring or synthetic polymer backbone and a phenol or aniline moiety improves not only the solubility of the polymer backbone, thus making it easy to handle, but also the reactivity of phenol-phenol bond or aniline-aniline bond, thus bringing about an increase in stability and mechanical strength.

It is therefore an object of the present invention to provide an in situ forming hydrogel which is superior in biostability and mechanical strength.

Technical Solution

In accordance with one aspect thereof, the present invention provides an injectable hydrogel, represented by the following Chemical Formula 2, in which two or more homogeneous or heterogeneous polymers, represented by the following Chemical Formula 1, are bonded to each other by a dehydrogenation reaction taking place between phenol or aniline moieties thereof on adjacent polymers, wherein the polymer backbone is grafted with the phenol or aniline moieties using a linker.

[Chemical Formula 1]

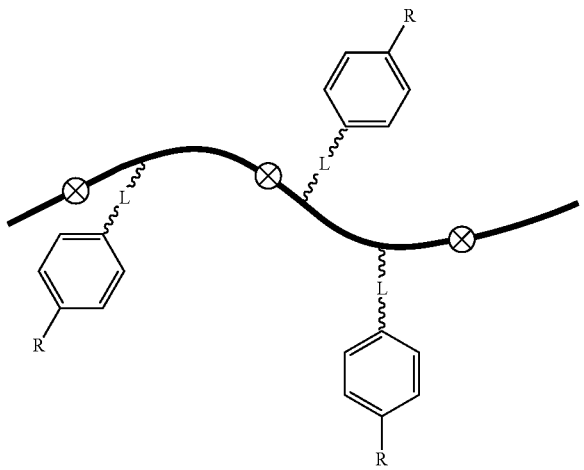

[Chemical Formula 2]

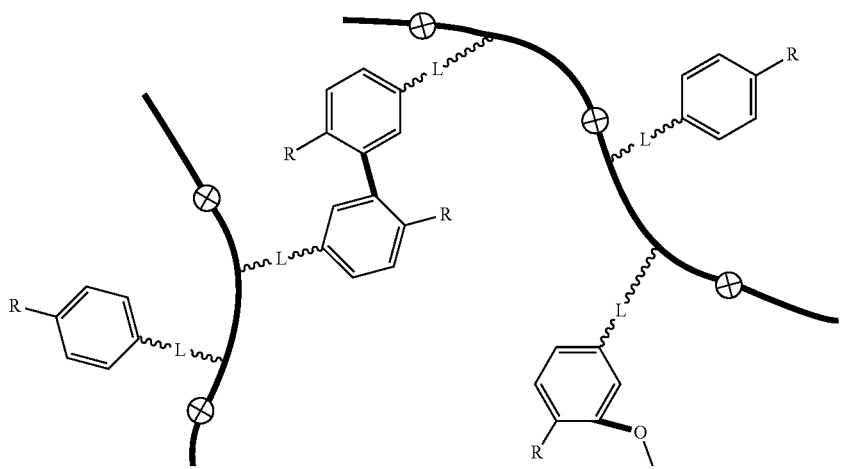

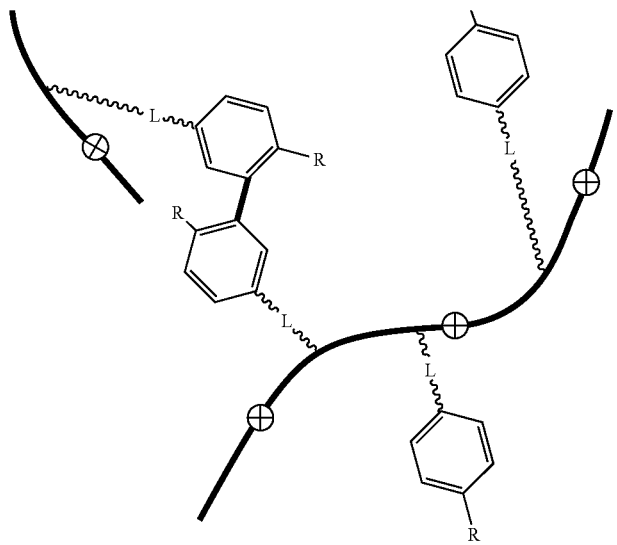

wherein,
R is hydroxyl or amine; and
L is a hydrophilic polymer chain (water-soluble polymeric linker).

In the presence of horseradish peroxidase and hydrogen peroxide, the polymers can be in situ cross-linked in vivo.

The polymer of Chemical Formula 1 may be prepared by grafting a phenol or aniline derivative represented by the following Chemical Formula 3 to a polymer backbone having amino, hydroxyl or carboxyl groups using an amide, urethane, urea or ester bond, with a hydrophilic polymer chain (water-soluble polymer) serving as a linker:

[Chemical Formula 3]

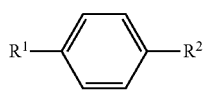

wherein,
$R^1$ is a hydroxyl group or an amine group; and
$R^2$ is a carboxyl group or an amine group.

For example, the polymer of Chemical Formula 1 can be prepared as illustrated in Reaction Schemes 1 to 5. In the reaction schemes, EDC stands for 1-ethyl-3-(3-dimethylaminopropyl)-carbodiimide, NHS for N-hydroxysuccinimide, TEA for triethylamine, DMAP for dimethylammonium pyridine, and NPCF for p-nitrophenylchloroformate.

In detail, the preparation of the polymer of Chemical Formula 1 may be achieved by (i) preparing a water-soluble polymer having hydroxyl or carboxyl groups as a linker; (ii) bonding either a phenol derivative or an aniline derivative to the linker to form a conjugate of linker-phenol or aniline derivative; and (iii) grafting a polymer backbone with the conjugate in such a manner as to directly link the linker to the backbone.

Optionally, the step of adding a succinic anhydride or NPCF together with TEA and DMAP may be conducted between the steps (i) and (ii).

The presence of EDC and HNS activates the phenol or aniline derivative to react with the hydrophilic polymer chain (water-soluble polymer). In addition, when the polymer backbone is grafted with the conjugate, EDC and HNS may be added to facilitate the reaction.

Before the step (iii), the conjugate may be further modified with a diamine compound.

[Reaction Scheme 1]

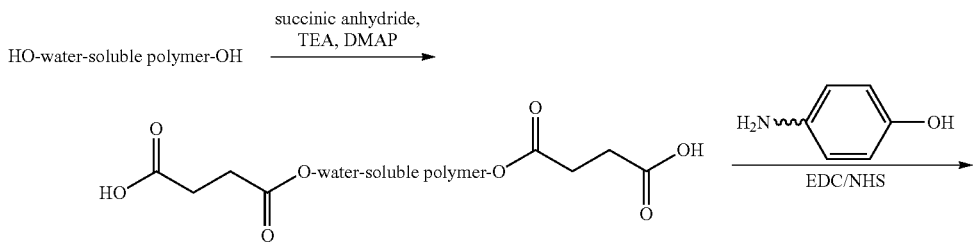

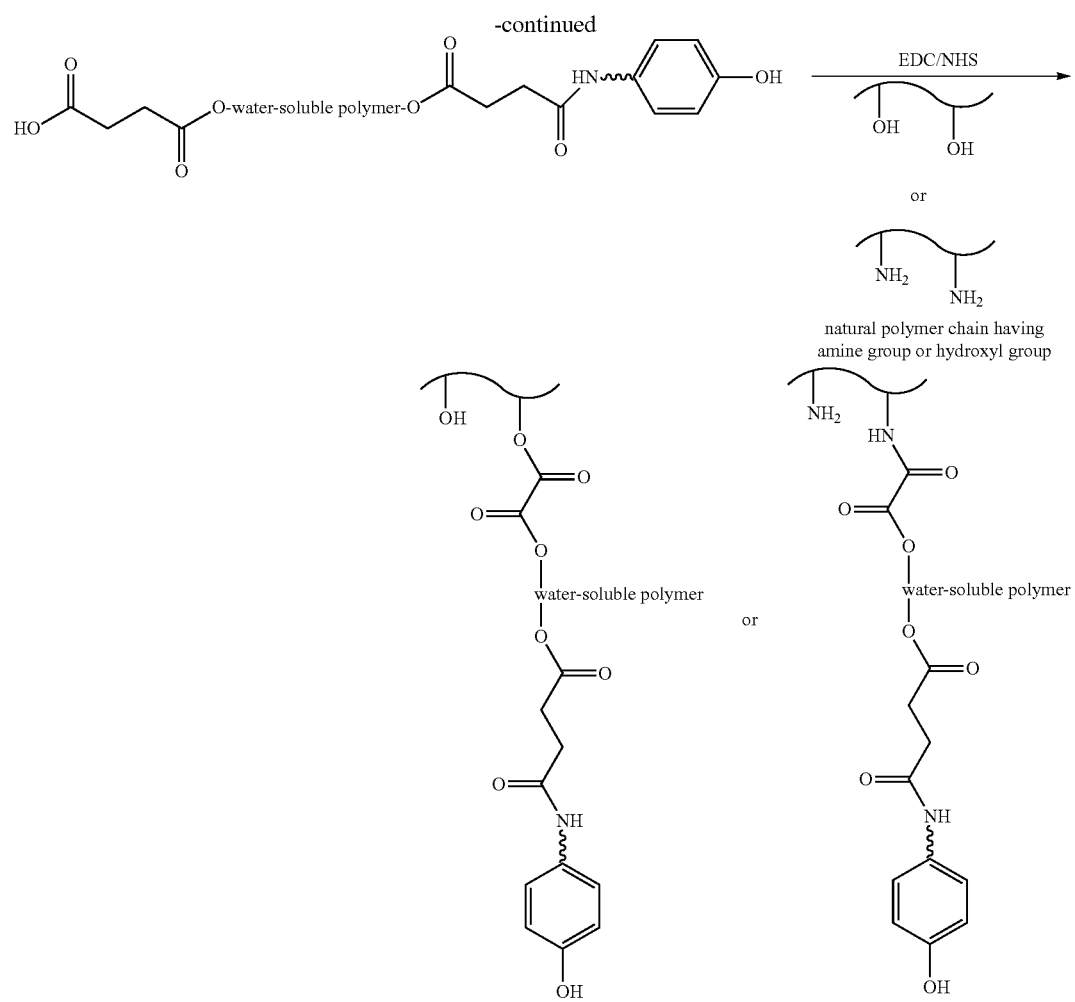
[Reaction Scheme 2]
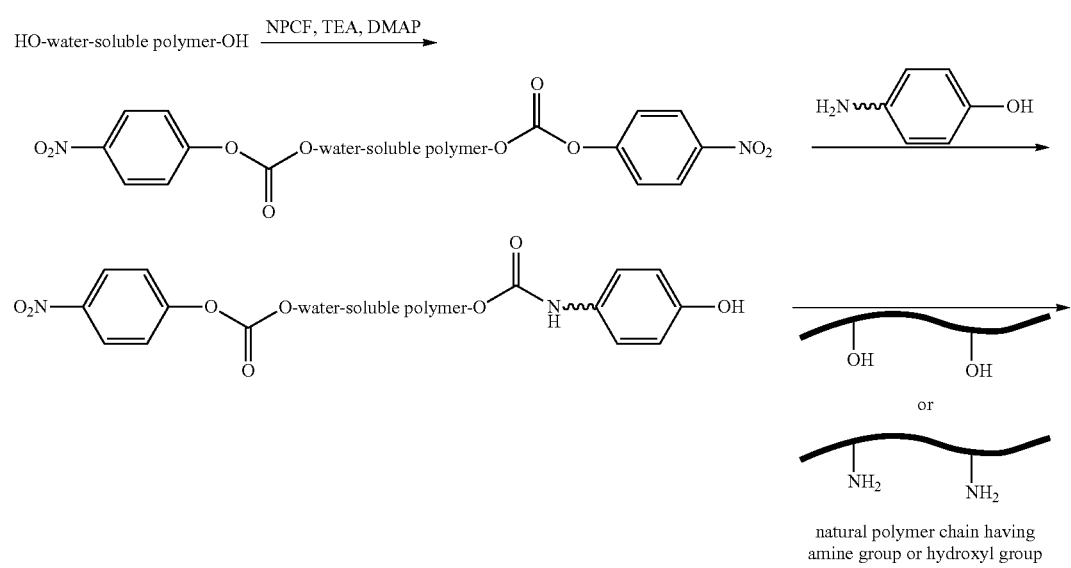

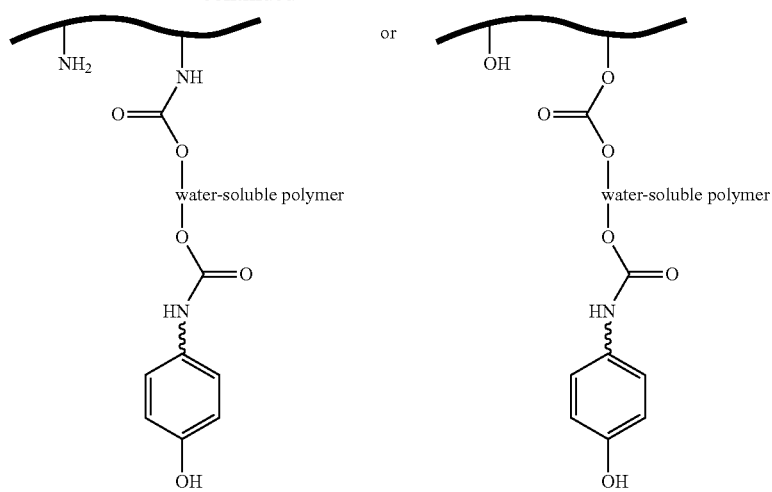
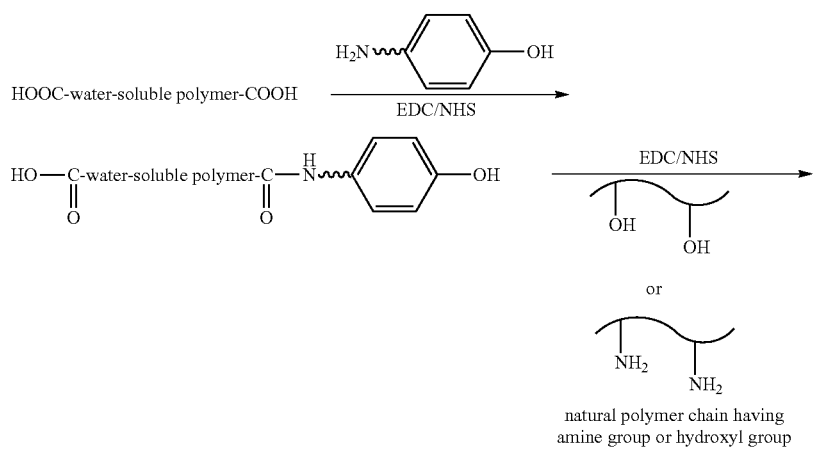
[Reaction Scheme 3]
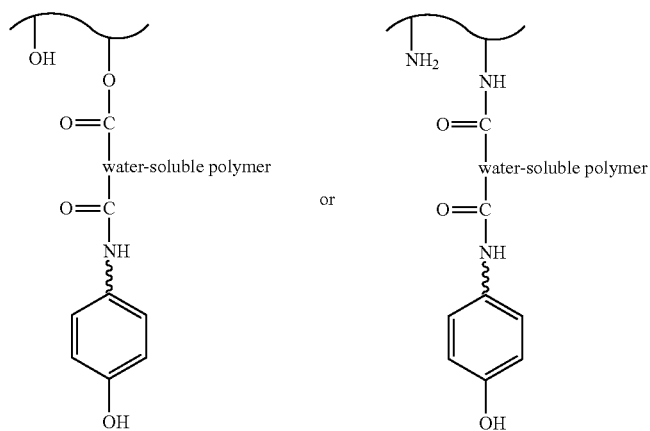

[Reaction Scheme 4]
HO-water-soluble polymer-OH →(NPCF, TEA, DMAP)
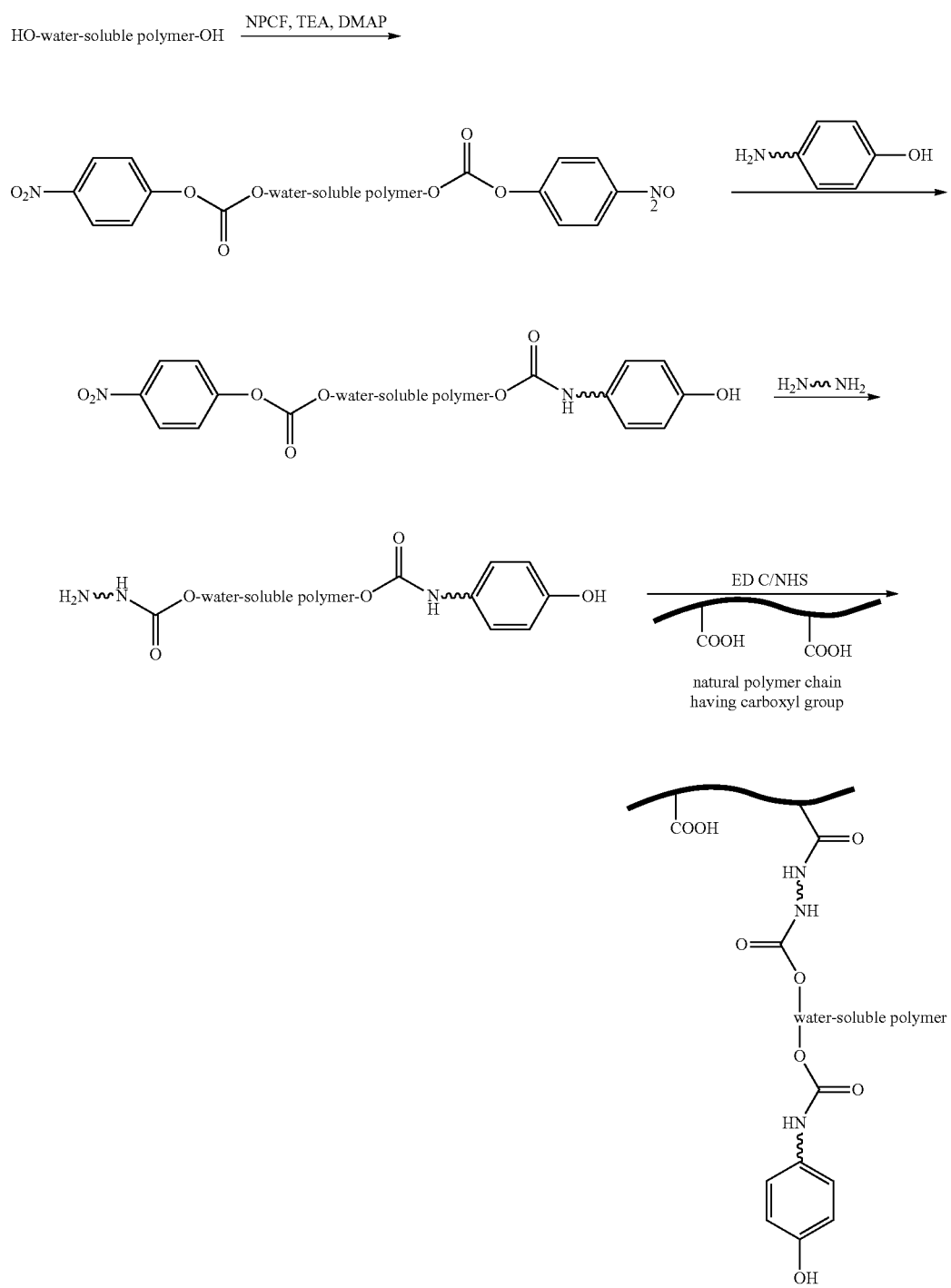
[Reaction Scheme 5]
H$_2$N-water-soluble polymer-NH$_2$ →(EDC/NHS)
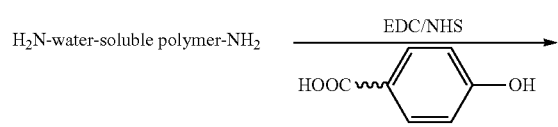

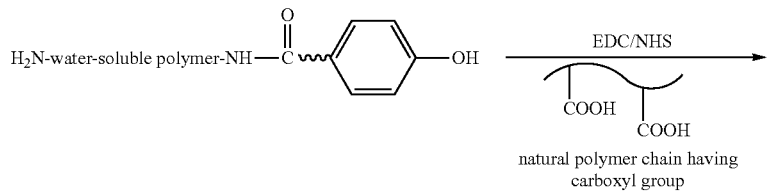 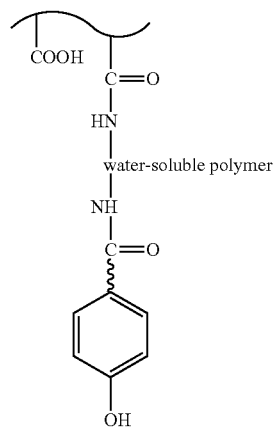

A polymer backbone suitable for use in the present invention may be selected from a group consisting of gelatin, chitosan, heparin, cellulose, dextran, dextran sulfate, chondroitin sulfate, keratan sulfate, dermatan sulfate, alginate, collagen, albumin, fibronectin, laminin, elastin, vitronectin, hyaluronic acid, fibrinogen, a multi-arm polymer and a combination thereof, but is not limited thereto.

The phenol derivative useful in the present invention is selected from the group consisting of tyramine, hydroxyphenylacetic acid, hydroxypropionic acid, derivatives thereof, and a combination thereof. One or more compounds selected from the group consisting of hydroxyethylaniline, aminoethylaniline, aminobenzylalcohol, and derivatives thereof may be used as the aniline derivative useful in the present invention.

As for the water-soluble polymer used as a linker in the present invention, it may be selected from the group consisting of polycationic, polyanionic, polyamphoteric, polynonionic, polypeptide, polyaliphatic, polyaromatic, polyester, polyanhydride, polyorthoester, polyurathane, and polyamide chain. Examples of the water-soluble polymers include polyethylene glycol (PEG), polyethylene oxide (PEO), polyethylenimine (PEI), polypropylene oxide (PPO), polyvinyl alcohol (PVA), poly(N-isopropylacrylamide) (polyNIPAAM), polyfumarate, polyorganophosphazene, polyacrylic acid (polyAAc), polyacrylsulfonate, poly hydroxyethyl-methacrylate(polyHEMA), and combinations thereof, but are not limited thereto. And, examples of the copolymers include PEO-PPO-PEO (Pluronic™ series), 4-arm PEO-PPO-PEO (Tetronic™ series), PEG-PEI, PEG-PVA, PEG-PEI-PVA, PEI-PVA, poly(NIPAAM-co-AAc), poly(NIPAAM-co-HEMA), and combinations thereof, but are not limited thereto.

As for the water-soluble polymer used as a linker in the present invention, it may be selected from the group consisting of a hydrophilic linear or multi-arm block copolymer selected from the group consisting of polyethylene glycol (PEG)-polylactic acid (PLA), polyethylene glycol(PEG)-polycarpropactone (PCL), polyethylene glycol(PEG)-poly(DL-lactic-co-glycolic acid) (PLGA), poly((propylene) fumarate), poly((ethylene)fumarate) and combinations thereof, but is not limited thereto.

The hydrogel according to the present invention can be customized in terms of physicochemical properties including gelation time, gel stability (time taken to degrade), mechanical strength and water content by controlling the concentration of horseradish peroxidase and hydrogen peroxide.

In addition, the molecular weight of the water-soluble polymer has an influence on the physicochemical properties of the hydrogel including gelation time, gel stability, mechanical strength and water content.

The hydrogel according to the present invention can be cross-linked in situ with the aid of a dual syringe kit or can be sprayed using a nozzle-mounted dual syringe kit. In addition, the hydrogel can be formed into sheets or discs using a dual syringe kit and a Teflon mold.

Further, the in situ forming injectable hydrogel according to the present invention may contain therein a biologically active substance having a phenol or aniline group. In a preferred embodiment, the biologically active substance is a peptide comprising tyrosine.

In accordance with another aspect thereof, the present invention provides an implant material for tissue regeneration and augmentation, comprising the injectable hydrogel of the present invention as an active ingredient.

Examples of the applications of the implant material include cartilage regeneration, bone regeneration, periodontal regeneration, skin regeneration, cardiac tissue regeneration, artificial intraocular lens, spinal cord regeneration, cranial regeneration, vocal regeneration and augmentation, adhesion barrier, urinary incontinence treatment, wrinkle removal, wound dressing, tissue augmentation and intervertebral disc treatment.

In accordance with a further aspect thereof, the present invention provides a carrier for delivering biologically active materials and drugs, comprising the in situ-forming injectable hydrogel as an active ingredient.

In a preferred embodiment, the biologically active materials or drugs may be peptide or protein drugs, anti-bacterial agents, anti-cancer agents, and/or anti-inflammatory agents.

Examples of the peptide or protein drugs include fibroblast growth factor (FGF), vascular endothelial growth factor (VEGF), transforming growth factor (TGF), bone morphogenetic protein (BMP), human growth hormone (hGH), pig growth hormone (pGH), granulocyte colony-stimulating factor (G-CSF), erythropoietin (EPO), macrophage colony-stimulating factor (M-CSF), tumor necrosis factor (TNF), epidermal growth factor (EGF), platelet-derived growth factor (PDGF), interferon-α,β,γ, interleukin-2 (IL-2), calcitonin, nerve growth factor (NGF), growth hormone releasing hormone, angiotensin, luteinizing hormone releasing hormone (LHRH), luteinizing hormone releasing hormone agonist (LHRH agonist), insulin, thyrotropin-releasing hormone (TRH), angiostatin, endostatin, somatostatin, glucagon, endorphine, bacitracin, mergain, colistin, monoclonal antibodies, and vaccines.

The anti-bacterial agents applicable to the present invention may be found among minocycline, tetracycline, ofloxacin, fosfomycin, mergain, profloxacin, ampicillin, penicillin, doxycycline, thienamycin, cephalosporin, nocardicin, gentamicin, neomycin, kanamycin, paromomycin, micronomicin, amikacin, tobramycin, dibekacin, cefotaxime, cefaclor, erythromycine, ciprofloxacin, levofloxacin, enoxacin, vancomycin, imipenem, and fusidic acid.

The anti-cancer agent applicable to the present invention may be selected from among paclitaxel, taxotere, adriamycin, endostatin, angiostatin, mitomycin, bleomycin, cisplatin, carboplatin, doxorubicin, daunorubicin, idarubicin, 5-fluorouracil, methotrexate, actinomycin-D, and combinations thereof.

Examples of the anti-inflammatory agents include acetaminophen, aspirin, ibuprofen, diclofenac, indometacin, piroxicam, fenoprofen, flubiprofen, ketoprofen, naproxen, suprofen, loxoprofen, cinnoxicam, and tenoxicam.

In accordance with an embodiment, gelatin, which is an enzymatically degradable, natural polymer, is used as a polymer backbone to which a phenol derivative is then attached using a water-soluble polymer, e.g., PEG, as a linker, to synthesize gelatin-PEG-tyramine (GPEG-TA). Thanks to the PEG linker, the in situ-forming, injectable hydrogel is improved in solubility, gelation time, mechanical strength and biostability, compared to a hydrogel prepared from the linker-free polymer, that is, gelatin-hydroxypehylacetic acid (GHPA).

The hydrogel according to the present invention finds a variety of applications in the biomedical field, including in situ-forming tissue engineering scaffolds; sustained release drug delivery systems for proteins, DNA, growth factors, cells, etc.; tissue augmentation; wound healing; and prevention of organ adhesion.

In greater detail, the hydrogel according to the present invention can be used as an artificial extracellular matrix to create a tissue engineering scaffold. A proper degradation rate is very important to adapt the hydrogel into an extracellular matrix because hydrogel, when used, may play an important role in the differentiation and growth of cells therein. For instance, gelatin is hydrolyzed specifically by matrix metalloprotenase (MMP), especially MMP-2 and MMP-9. The hydrogel matrix containing gelatin is degraded by the enzymes and then reformed into an extracellular matrix (ECM) secreted by cells, so that the cells within the hydrogel can effectively grow and differentiate.

Also, when the hydrogel is used as a tissue engineering scaffold, its matrix stiffness has a large influence on the growth and differentiation of cells located inside the gel. The necessary matrix stiffness differs from one type of cell to another. For instance, osteocytes are known to grow well on stiff matrixes whereas soft tissue cells, e.g., fibroblasts, myoblasts, etc., require a soft matrix for their growth. In a system using an enzymatic reaction, the degree to which the hydrogel is crosslinked can be easily controlled by the quantity of hydrogen peroxide and therefore, the stiffness of the hydrogel can be manipulated.

In an embodiment, the hydrogel according to the present invention may be used as an artificial extracellular matrix suitable for use as a drug delivery scaffold. For instance, when tyramine is introduced therein, heparin (that can bind physically with various growth factors) can retain growth factors and allows the sustained release of the growth factors (growth factor binding sites). Phenol-modified cell adhesion peptides or proteins, for example, RGDY or YIGSR, may be used to increase cell adhesion inside the hydrogel matrix. Ingredients effective for cell growth and differentiation may be introduced into the hydrogel through an enzymatic mechanism to prepare an in situ-forming artificial ECM.

Advantageous Effects

As described above, the introduction of a water-soluble polymer, such as PEG, as a linker between a naturally occurring or synthetic polymer backbone and a phenol or aniline moiety improves not only the solubility of the polymer backbone, thus making it easy to handle, but also the reactivity of phenol-phenol bond or aniline-aniline bond, thus bringing about an increase in gel stability and mechanical strength. In addition, the hydrogel according to the present invention finds a variety of applications in the biomedical field.

BRIEF DESCRIPTION OF DRAWINGS

The above and other objects, features and advantages of the present invention will be more clearly understood from the following detailed description taken in conjunction with the accompanying drawings, in which.

BEST MODE FOR CARRYING OUT THE INVENTION

In an embodiment of the present invention, gelatin is adapted as a polymer backbone which is grafted with the phenyl derivative tyramine using PEG as a linker to synthesize gelatin-PEG-tyramine (GPEG-TA) polymers. These polymers can be in situ crosslinked by an enzymatic reaction to afford an in situ-forming hydrogel.

The introduction of PEG as a linker improves the solubility of the polymers and increases the reactivity of tyramine as well. As a result, the hydrogel thus obtained has greater advantages in light of biostability and mechanical strength compared to the hydrogel lacking the linker. For purposes of comparison, gelatin-hydroxyphenylacetic acid (GHPA) is used as a control in assaying physicochemical properties of hydrogels with or without linkers.

In the in situ forming GPEG-TA hydrogel, gelatin plays a role as a substrate for proteineous degradation, especially by MMP. The physicochemical properties of GPEG-TA hydrogel, such as gelation time, gel stability, swelling and mechanical strength, were determined for different hydrogen peroxide levels. Particularly, in vitro cellular activity was assayed to determine the biocompatibility of GPEG-TA. Animal experiments were conducted to assay the GPEG-TA hydrogel for biostability and tissue regeneration including cartilage regeneration, vocal regeneration and augmentation, prevention of organ adhesion, spinal cord regeneration, intervertebral disc treatment, and bone regeneration.

MODE FOR INVENTION

A better understanding of the present invention may be obtained by means of the following examples which are set forth to illustrate, but are not to be construed as limiting the present invention.

PREPARATION EXAMPLE 1

Synthesis of Gelatin-PEG-Tyramine (GPEG-TA)

Figure 1:
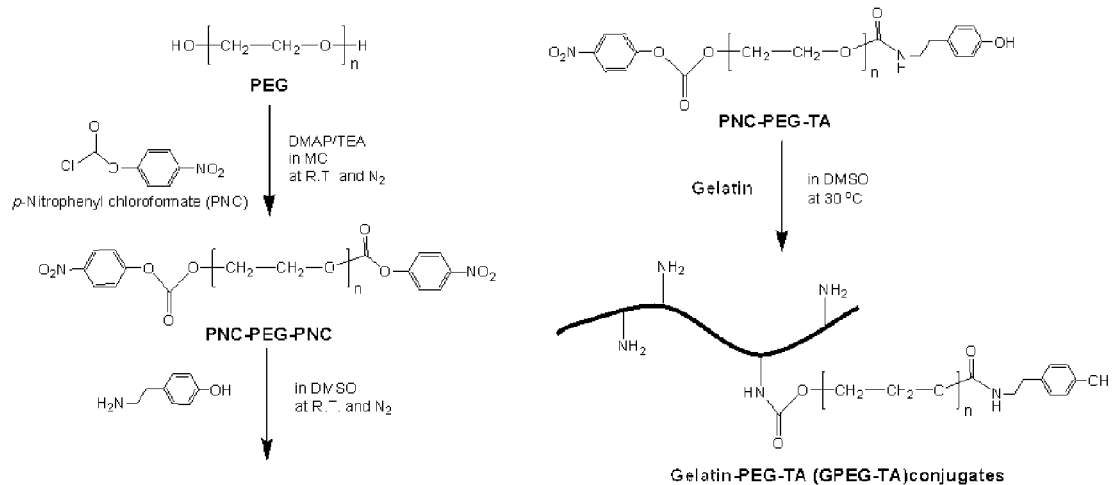
FIG. 1 is a reaction scheme showing the synthesis of GPEG-TA.

FIG. 1 is a reaction scheme for the synthesis of a GPEG-TA copolymer.

1. Synthesis of Poly(Ethyleneglycol)-(P-Nitrophenyl Chloroformate) (PEG-NPCF)

A solution of 10 g (2.9 mmol) of PEG in 100 mL of methylene chloride (MC) was mixed sequentially with a solution of 0.779 g (6.38 mmol) of DMAP and 0.645 g (6.38 mmol) of TEA in 10 mL of MC and a solution of 1.286 g (6.38 mmol) of NPCF in 50 mL of MC. The molar ratio of PEG:DMAP:TEA:NPCF was 1:2.2:2.2:2.2. The reaction was performed at 30° C. for 24 hrs in a nitrogen atmosphere.

After completion of the reaction, a filter was used to filter the reaction mixture and remove unreacted reagents and the reaction mixture was then concentrated using a rotary evaporator. The concentrate was dropwise added to 1600 mL of chilled ether to form precipitates which were then obtained by filtration. The filtrate thus obtained was allowed to stand for 24 hrs in a vacuum oven to remove the remaining organic solvents to afford the desired compound (PEG-NPCF) as a white powder.

2. Synthesis of GPEG-TA

To a solution of 5 g (1.471 mmol) of PEG-NPCF in 100 mL of dimethylsulfoxide (DMSO) was added a solution of 0.202 g (1.471 mmol) of tyramine (TA) in 50 mL of DMSO, with the molar ratio of PEG-NPCF:TA being 1:1. A reaction was conducted at 30° C. for 6 hrs in a nitrogen atmosphere. Thereafter, a gelatin solution (1 g/200 ml in DMSO) was added, followed by reaction at 30° C. for 24 hrs in a nitrogen atmosphere.

After completion of the reaction, the reaction mixture was subjected to membrane dialysis against water (cutoff Mw 6000-8000 Da) to remove unreacted PEG-TA. The dialyzed solution was lyophilized to produce the desired compound (GPEG-TA) as a white powder. On a $^1$H NMR spectrum, peaks appeared at 6.91-7.23 ppm which correspond to the TA substituents, confirming the synthesis of GPEG-TA.

PREPARATION EXAMPLE 2

Synthesis of Gelatin-Hydroxyphenylacetic Acid (GHPA)

Figure 2:
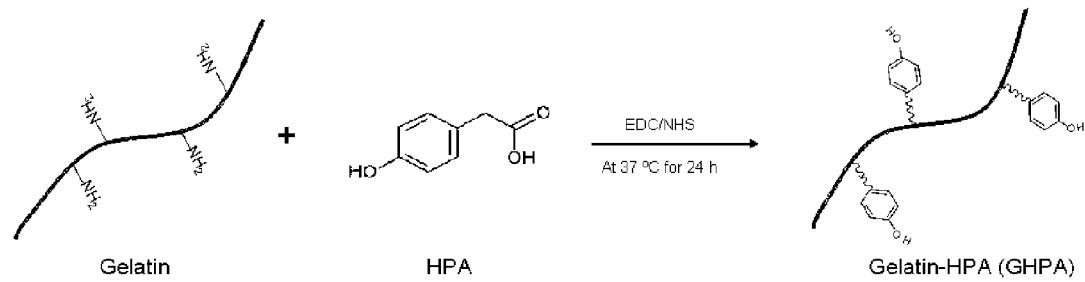
FIG. 2 is a reaction scheme showing the synthesis of GHPA.

FIG. 2 is a reaction scheme showing the synthesis of GHPA.

10 Grams of gelatin was dissolved in 200 mL of 0.1 M 2-(N-morpholino)ethanesulfonic acid (MES) to prepare solution A. Separately, 0.609 g of (4 mmol) of 4-hydroxyphenylacetic acid (HPA) was dissolved in 50 mL of 0.1 M MES to furnish solution B. 0.92 Grams (4.8 mmol) of 1-ethyl-3-(3-dimethylaminopropyl)-carbodiimide (EDC) and 0.276 g (2.4 mmol) of N-hydroxysuccinimide (NHS) were each dissolved in 5 mL of 0.1 M MES.

The EDC solution and the NHS solution were sequentially at intervals of 15 min to the solution B. 15 Min after addition of the NHS solution, the solution B activated with EDC/NHS was mixed with the solution A. The reaction was performed at 40° C. for 24 hrs.

After completion of the reaction, the reaction mixture was filtered through a syringe filter (450 nm). Then, the filtrate was subjected to membrane dialysis against distilled water (cutoff Mw. 3500 Da) for 3~4 days, followed by freeze drying to afford GHPA as a white powder. The chemical structure of the synthesized GHPA was identified by $^1$H NMR analysis. On the spectrum, peaks appeared at 6.91-7.23 ppm which correspond to the TA substituents, confirming the synthesis of GHPA.

EXAMPLE 1

Preparation of GPEG-TA Hydrogel Using Enzymatic Reaction

A solution of GPEG-TA in HRP (solution A) was mixed with a solution of GPEG-TA in $H_2O_2$ (solution B) to prepare a hydrogel. The polymer solutions were controlled to have a final concentration of from 1 to 20 wt % and were applied in various forms using a dual syringe kit or a spray kit or by Teflon molding.

GHPA and CHPA, GPEG-TA, or CPEG-TA was dissolved in $H_2O_2$ (solution B) and mixed with a solution of Tet-TA/DA in HRP (solution A) to prepare a hydrogel.

GHPA hydrogel could have been prepared in the same manner. However, it was possible to control the final concentration of GHPA to range only between 5 and 10 wt %. At a concentration of 10 wt %, it was practically difficult to deal with the polymer solutions due to high viscosity. In contrast, GPEG-TA, a polymer with PEG introduced thereinto, was highly soluble in water and thus the polymer solutions were comparably easy to manage thanks to the low viscosity thereof.

Figure 3:
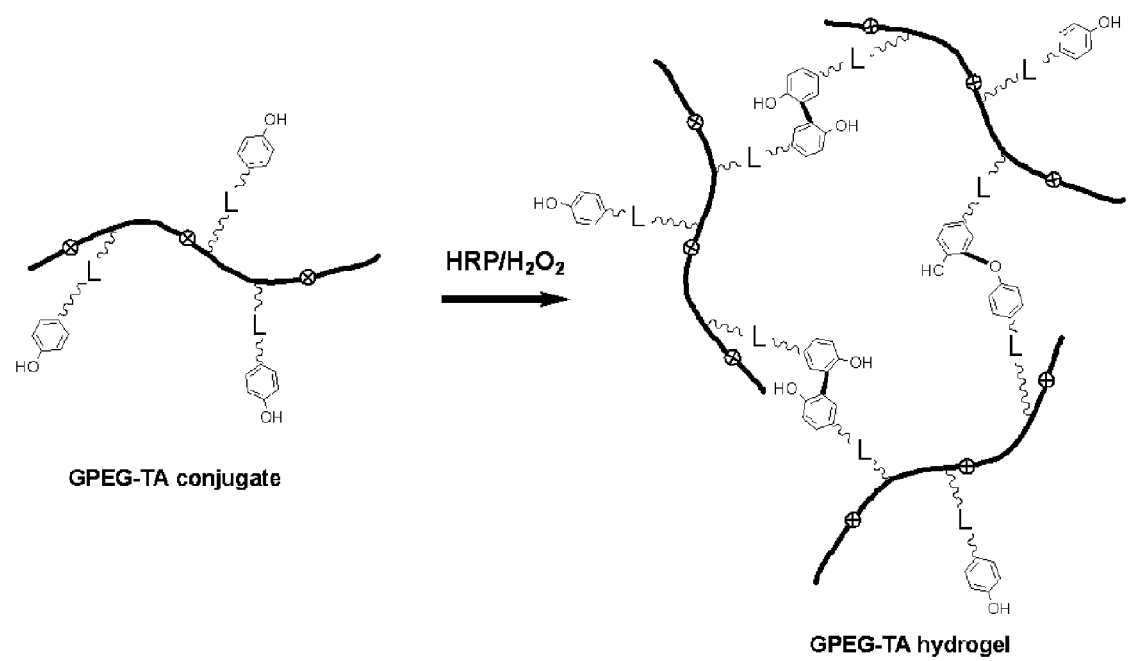
FIG. 3 is a reaction scheme showing the synthesis of a GPEG-TA hydrogel on the basis of enzymatic reactions.

FIG. 3 is a reaction scheme showing the enzymatic preparation of GPEG-TA hydrogel.

EXAMPLE 2

Preparation of an In Situ-Forming Hydrogel Using a Dual Syringe Kit

Figure 4:
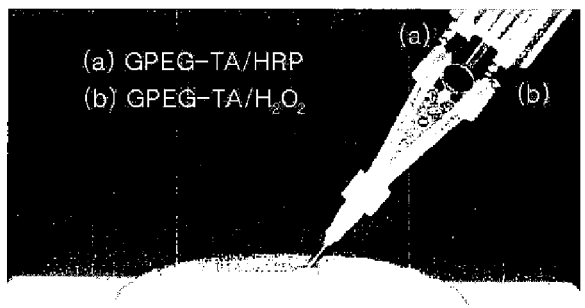
FIG. 4 is a photograph showing the formation of in situ-forming hydrogel using a dual syringe kit.

Using a dual syringe kit, a solution of GPEG-TA in HRP (solution A) was mixed with a solution of GPEG-TA in $H_2O_2$ (solution B) to form an in situ-forming hydrogel. In this regard, solution A and solution B were placed in respective syringes. FIG. 4 is a photograph showing the preparation of an in situ-forming hydrogel using a dual syringe kit.

EXAMPLE 3

Preparation of Spray-Type Hydrogel Using a Dual Syringe Kit and a Spraying Kit

Figure 5:
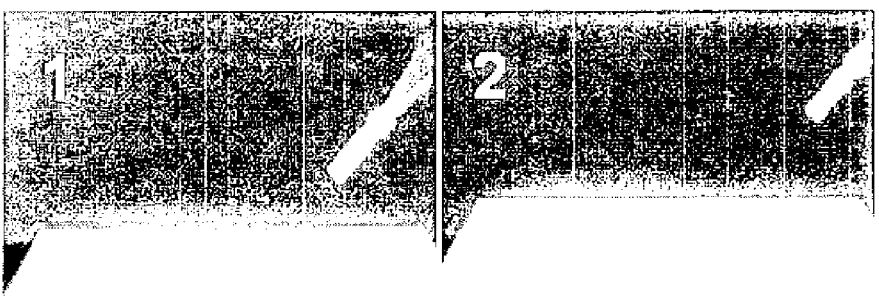
FIG. 5 is a set of photographs showing the formation of hydrogel using a dual syringe kit equipped with a spraying nozzle.

Solutions of GPEG-TA in HRP (solution A) and a solution of GPEG-TA in $H_2O_2$ (solution B) were each placed in separate syringes to give a dual syringe kit which was mounted with spraying nozzles. The solutions were sprayed using the kit to form hydrogel. FIG. 5 is a set of photographs showing the preparation of the hydrogel using the dual syringe kit with the mounted spraying nozzles.

EXAMPLE 4

Formation of Hydrogel Sheet and Disc Using Teflon Mold

Figure 6:
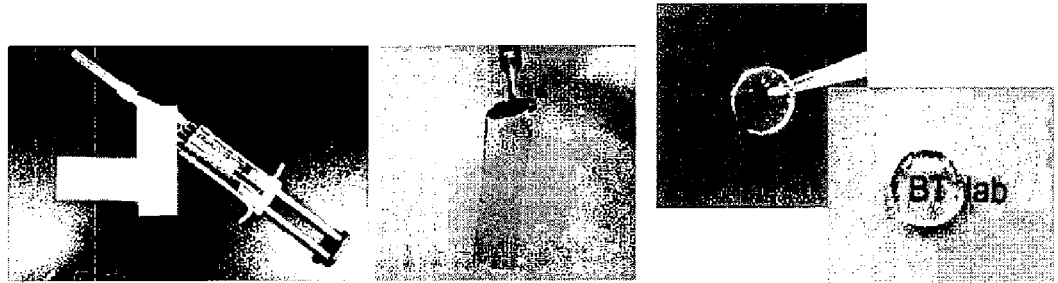
FIG. 6 is a set of photographs showing the formation of GPEG-TA into a sheet or a disc using a Teflon mold.

A solution of GPEG-TA in HRP (solution A) and a solution of GPEG-TA in $H_2O_2$ were each placed in the separate syringes of a dual syringe kit and were introduced into a Teflon mold to form hydrogel sheets and discs. FIG. 6 is a set of photographs showing the formation of GPEG-TA hydrogel sheets and discs using a Teflon mold.

EXPERIMENTAL EXAMPLE 1

Biocompatibility of GPEG-TA Hydrogel to 2D Cells

For use in an in vitro biocompatibility assay, GPEG-TA hydrogel discs were prepared using a Teflon mold in the same manner as in Example 4. Cells of various types were cultured on the hydrogel discs to conduct assays for cell adhesion and proliferation. The hydrogels used in the assays had a concentration of 5 wt % and a mechanical strength of 2700 Pa.

Myoblasts (CSC12), osteoblasts (MC3T3) and rat mesenchymal stem cells (MSC) were employed for the biocompatibility assay. The cells were cultured at a density of $1 \times 10^5$ cells/well on the hydrogel discs and analyzed using a live/dead assay under a phase contrast microscope.

Figure 7:
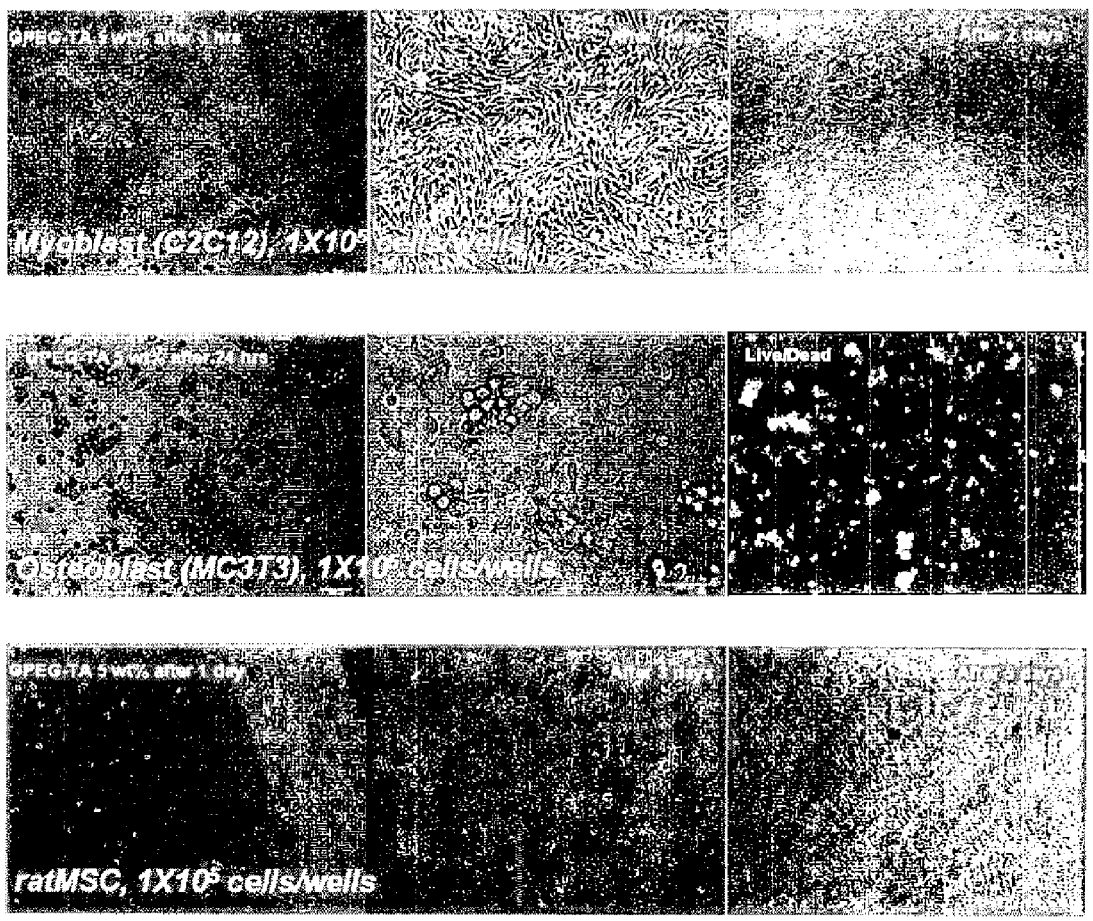
FIG. 7 is a set of microphographs showing 2D cell adhesion and proliferation in GPEG-TA hydrogel.

The results are shown in FIG. 7. As shown in this figure, all cells were found to adhere well to and greatly proliferate on the discs, demonstrating the in vitro biocompatibility of the GPEG-TA hydrogel. In contrast, GHPA hydrogel collapsed within 24 hrs due to its significantly low stability compared to that of GPEG-TA hydrogel, so that biocompatibility assays could not be performed.

The excellent stability of GPEG-TA hydrogel was thought to be attributed to the introduction of PEG, which increased the reactivity of tyramine to improve the degree of crosslinking of the polymers, resulting in excellent stability. Together with excellent biocompatibility to various cells, the stability allows the GPEG-TA hydrogel to be applied to the regeneration of various tissues.

EXPERIMENTAL EXAMPLE 2

Assay of GPEG-TA Hydrogel for 3D Cell Adhesion and Proliferation

A 3D cell encapsulation experiment was conducted using GPEG-TA hydrogel. In this regard, a solution of GPEG-TA in HRP (solution A) and a solution of GPEG-TA in $H_2O_2$ (solution B) were prepared, and cells were blended with solution A. The cell-loaded solution A was mixed with an equal amount of solution B to form a hydrogel, followed by cell incubation for 7 days.

The hydrogel thus obtained had a final concentration of 5 wt %. Human cardiac progenitor cell (hCPC) and rat MSC were cultured at a density of $5 \times 10^4$ cells/well. After culturing, the cells were analyzed using an F-actin and a live/dead assay.

Figure 8:
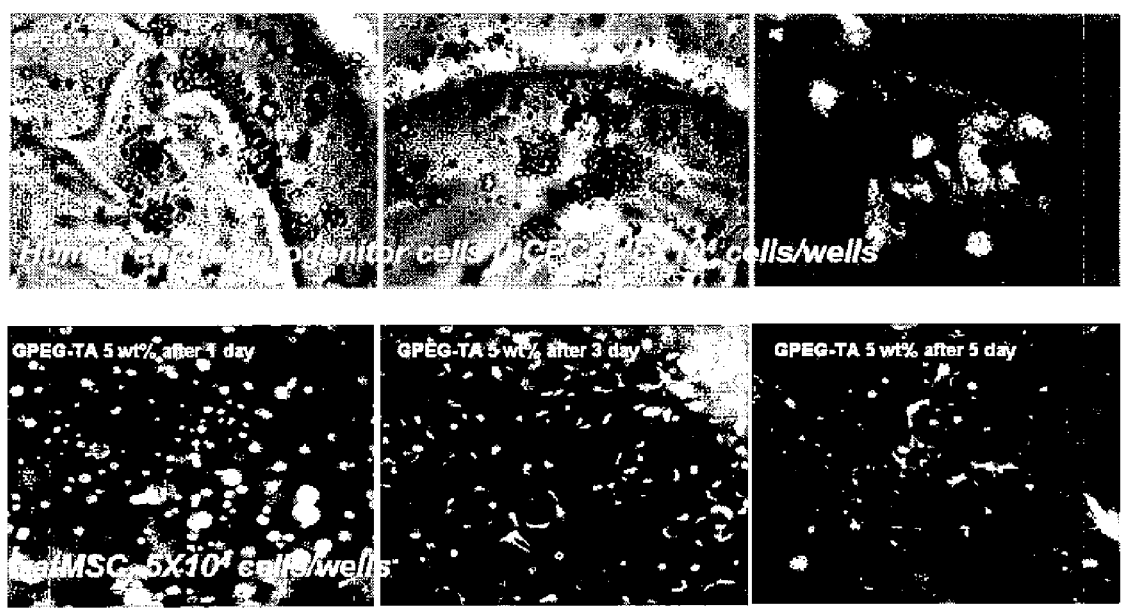
FIG. 8 is a set of photographs showing 3D cell adhesion and proliferation in GPEG-TA hydrogel.

As shown in FIG. 8, the 3D encapsulated cells were observed to effectively adhere to and proliferate within the hydrogel matrix, indicating that GPEG-TA hydrogel is useful for the effective 3D growth of various cells and the regeneration of various tissues.

EXPERIMENTAL EXAMPLE 3

Assay of GPEG-TA Hydrogel for In Vivo Stability

GPEG-TA hydrogel was assayed for in vivo stability in white rabbits. For experiments, a solution of GPEG-TA in HRP (solution A) and a solution of GPEG-TA in $H_2O_2$ (solution B) were prepared, followed by obtaining a dual syringe kit in the same manner as in Example 2. The transdermal injection of the solutions was done to white rabbits using the dual syringe kit. After transplantation had been in place for two weeks, the tissues were excised and stained with H&E to analyze inflammation and infiltration.

Figure 9:
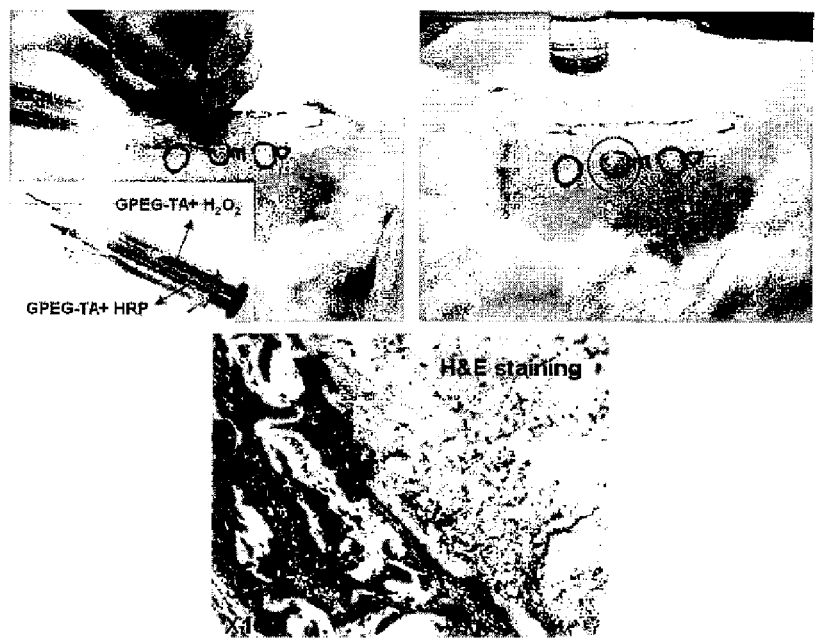
FIG. 9 is a set of photographs showing the in vivo stability of GPEG-TA hydrogel.

As seen in FIG. 9, surrounding tissues infiltrated the injected GPEG-TA and grew therein, with neither inflammation nor alloplastic reactions, indicating that GPEG-TA hydrogel has excellent in vivo stability and is useful in tissue regeneration in addition to being applicable to in situ forming implantation.

EXPERIMENTAL EXAMPLE 4

In Vivo Assay of GPEG-TA Hydrogel for In Vivo Human Growth Hormone (hGH) Release Behavior The in situ forming GPEG-TA hydrogel was assayed in vivo for human growth hormone (hGH) release behavior. S.D. rats (5-6 weeks old) were employed as experimental animals.

A dual syringe kit was constructed in the same manner as in Example 2, with the exception that human growth hormone (hGH) was mixed with solution A. Using the kit, the hormone was transdermally injected into the rats and incubated for 2 weeks.

Figure 10:
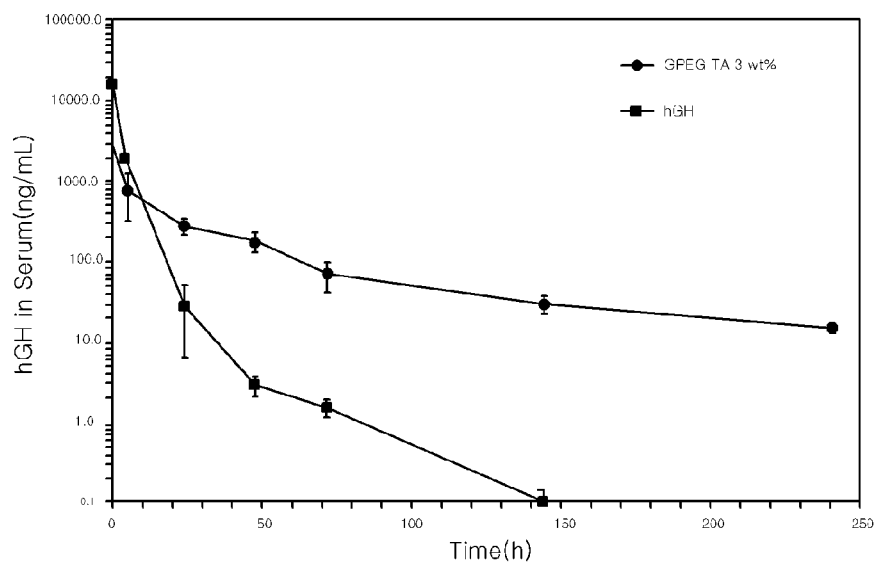
FIG. 10 is a graph showing the human growth hormone (hGH) release behavior of GPEG-TA hydrogel.

As depicted in FIG. 10, the hGH was observed to be released in a sustained manner in the animals while the GPEG-TA hydrogel had completely degraded within 2 weeks. In addition, the release rate could be controlled by varying the concentrations of hydrogen peroxide or the polymer. Consequently, the in situ forming GPEG-TA hydrogel was found to be useful as a carrier for delivering hGH.

EXPERIMENTAL EXAMPLE 5

Assay of GPEG-TA Hydrogel for Cartilage Regeneration

The in situ-forming GPEG-TA hydrogel was assayed for cartilage regeneration. The assay was conducted with GPEG-TA hydrogel, GPEG-TA hydrogel with chondrocytes loaded therein, and GPEG-TA hydrogel with TGF-β3 and chondrocytes loaded therein and in a control (defect only).

In this regard, dual syringe kits were constructed in the same manner as in Example 2, with the exception that chondrocytes alone or in combination with TGF-β3 were mixed with solution. A. Using the kits, the solutions were injected into the cartilage of white rabbits and incubated for four weeks.

Figure 11:
FIG. 11 is a set of photographs showing the effect of GPEG-TA hydrogel on cartilage regeneration.

The results are given in FIG. 11. As seen in these photographs, the cartilage was effectively regenerated in all of the experimental groups, indicating that the in situ-forming GPEG-TA hydrogel can be effectively applied to cartilage regeneration.

EXPERIMENTAL EXAMPLE 6

Assay of GPEG-TA Hydrogel for Spinal Cord Regeneration

The in situ-forming GPEG-TA hydrogel was assayed for spinal cord regeneration. In this regard, a dual syringe kit was constructed in the same manner as in Example 2. A hemisection was performed on the spinal cord of rats, after which the hydrogel was injected into the lesion using the dual syringe kit and the animals were observed for two weeks.

Figure 12:
FIG. 12 is a set of photographs showing the effect of GPEG-TA hydrogel on spinal cord regeneration.
Figure 12:

The results are shown in FIG. 12. As can be seen, the in situ-forming GPEG-TA hydrogel filled up the lesion. Two weeks after injection, the tissues were excised and subjected to immunohistochemical staining. The immunostaining results indicated that the spinal cord tissue was regenerated with the injected GPEG-TA hydrogel being very well fused with surrounding host tissues.

Therefore, the in situ-forming GPEG-TA hydrogel can be effectively applied to spinal cord regeneration.

EXPERIMENTAL EXAMPLE 7

Assay of GPEG-TA Hydrogel for Vocal Cord Regeneration and Augmentation

The in situ-forming GPEG-TA hydrogel was assayed for vocal cord regeneration and augmentation. In this regard, a dual syringe kit was constructed in the same manner as in Example 2, with the exception that chondrocytes were mixed with solution A.

Using the dual syringe kit, the chondrocytes mixed with the solution were implanted into the vocal cords of white rabbits which were then observed for one month. During the implantation, the animals were CT photographed. The CT images demonstrated vocal regeneration and augmentation. After being excised, the vocal tissues were examined for inflammation and immune reactions and used in RT-PCT and Western blotting to quantitatively determine the proliferation of chondrocytes and the extent of vocal regeneration.

Figure 13:
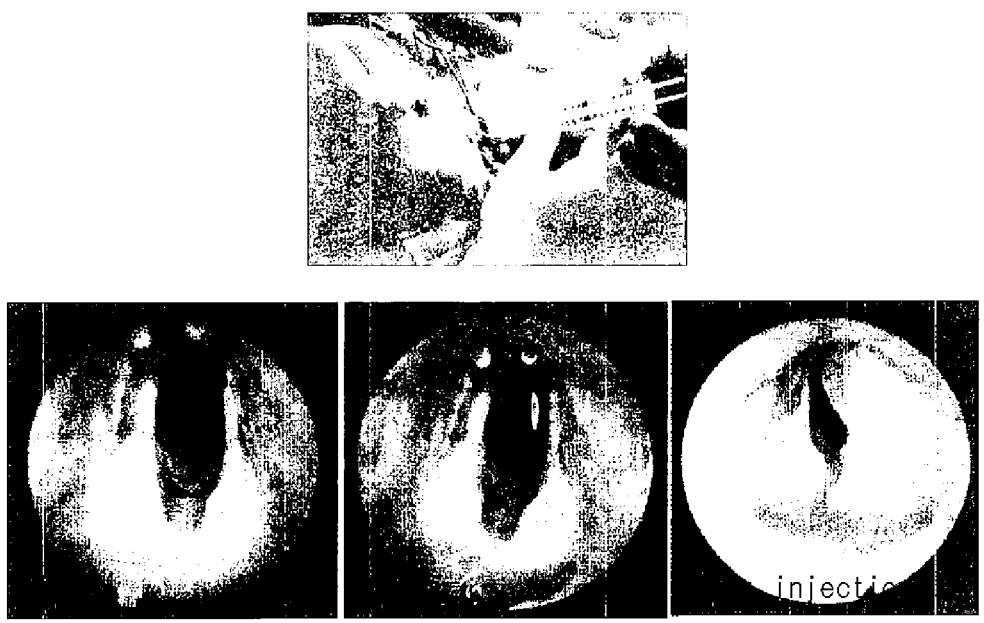
FIG. 13 is a set of photographs showing the effect of GPEG-TA hydrogel on vocal regeneration and augmentation.

Therefore, as shown in FIG. 13, the in situ-forming GPEG-TA hydrogel can be effectively applied to vocal regeneration and augmentation.

EXPERIMENTAL EXAMPLE 8

Assay of GPEG-TA Hydrogel for Prevention of Organ Adhesion

The in situ-forming GPEG-TA hydrogel was assayed for ability to prevent organ adhesion. To this end, a spraying, dual syringe kit was constructed in the same manner as in Example 3. Rats were employed as experimental animals. The animal models were injured at the caecum and the peritoneum and the hydrogel was applied to the injured site using the spraying, dual syringe kit. Two weeks after the application, the rats were underwent a laparotomy so that organ adhesion and alloplastic reactions could be examined.

Figure 14:
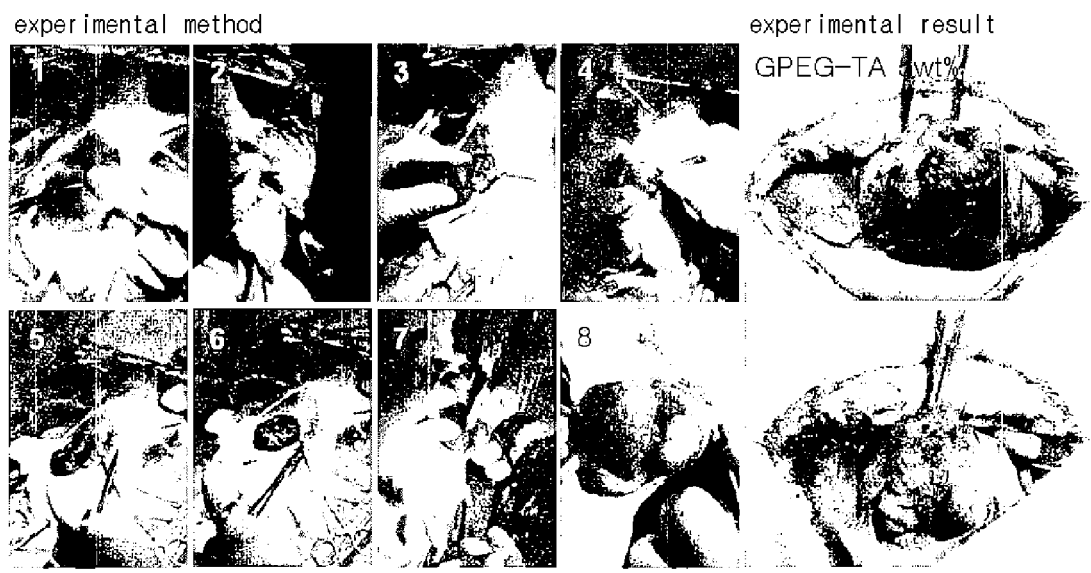
FIG. 14 is a set of photographs showing the effect of GPEG-TA on the prevention of organ adhesion.

As seen in FIG. 14, neither organic adhesions, nor specific inflammations and alloplastic reactions were observed, demonstrating that the in situ-forming GPEG-TA hydrogel can be effectively used as a medium for preventing organ adhesions.

EXPERIMENTAL EXAMPLE 9

Assay of GPEG-TA Hydrogel for Intervertebral Disc Regeneration

Figure 15:
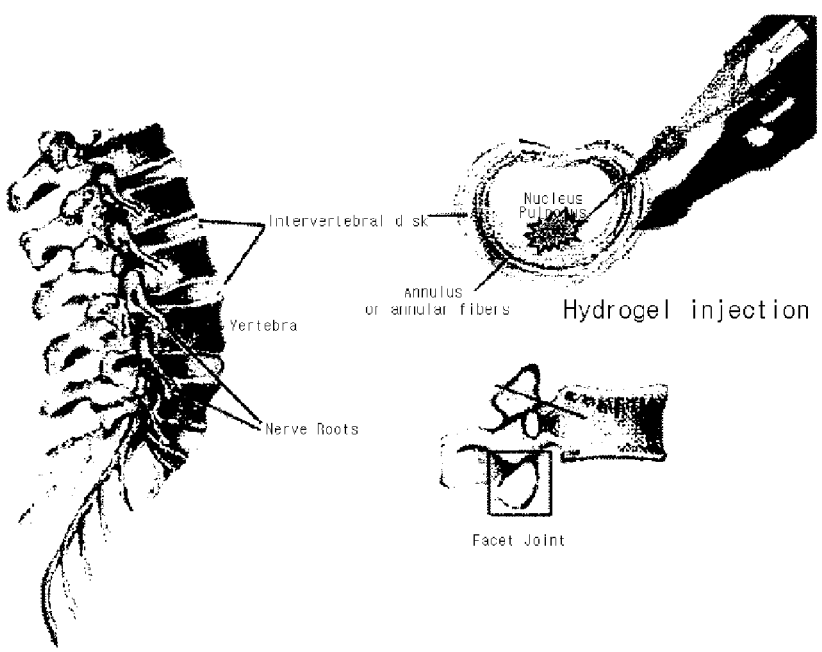
FIGS. 15 and 16 are a diagram and a set of photographs showing the use of GPEG-TA in intervertebral regeneration.
Figure 16:
Figure 16:
Figure 16:
Figure 16:

The in situ-forming GPEG-TA hydrogel was assayed for intervertebral disc regeneration as illustrated in FIGS. 15 and 16. In this regard, a dual syringe kit was constructed in the same manner as in Example 2. Pigs were employed as animal models. Using the dual syringe kit, the hydrogel was injected into the intervertebral disc (nucleus pulposus), followed by monitoring for one month.

During the implantation, the animals were monitored for nucleus pulposus regeneration with MRI. Thereafter, the tissues were excised and examined for inflammation and immune reactions. Histochemical staining and RT-PCR were performed to quantitatively determine the regeneration of the nucleus pulposus.

Taken together, the data obtained from the experiments demonstrated that the in situ-forming GPEG-TA hydrogel can be effectively applied to the treatment of lumber herniated intervertebral discs.

EXPERIMENTAL EXAMPLE 10

Assay of GPEG-TA Hydrogel for Bone Regeneration

The in situ-forming GPEG-TA hydrogel was assayed for bone regeneration. In this end, a dual syringe kit was constructed in the same manner as in Example 2, with the exception that an organic material effective for oeteogenesis, such as hydroxy apatite or tricalcium phosphate, and a growth factor for bone morphogenesis, such as bone morphogenetic protein (BMP) or Transforming growth factor (TGF), were mixed with solution A.

Rats were injured to form defects on the skull. Using the dual syringe kit, the hydrogel was formed in the sites of the defects and observed for 1-2 months. During the implantation term, the animal models were monitored for bone regeneration with CT imaging. Thereafter, the tissues were excised to examine inflammation and immune reactions, and bone regeneration was quantitatively determined using histochemical staining and calcium analysis.

Taken together, the data obtained through the experiments demonstrated that the in situ-forming GPEG-TA hydrogel can be effectively applied to bone regeneration.

EXPERIMENTAL EXAMPLE 11

Gelation Time of GPEG-TA and GHPA Hydrogels Depending on Enzyme Level

GPEG-TA and GHPA hydrogels were evaluated for gelation time at various HRP concentrations. To this end, solution A and solution B were prepared in the same manner as in Example 1, with the exception that various concentrations of HRP were used for solution A. The two solutions were mixed using the same quantity for each one to prepare hydrogels.

The time period taken for the mixture to cease to flow was measured using a vial tilting method and this was regarded as the gelation time of hydrogel.

Figure 17:
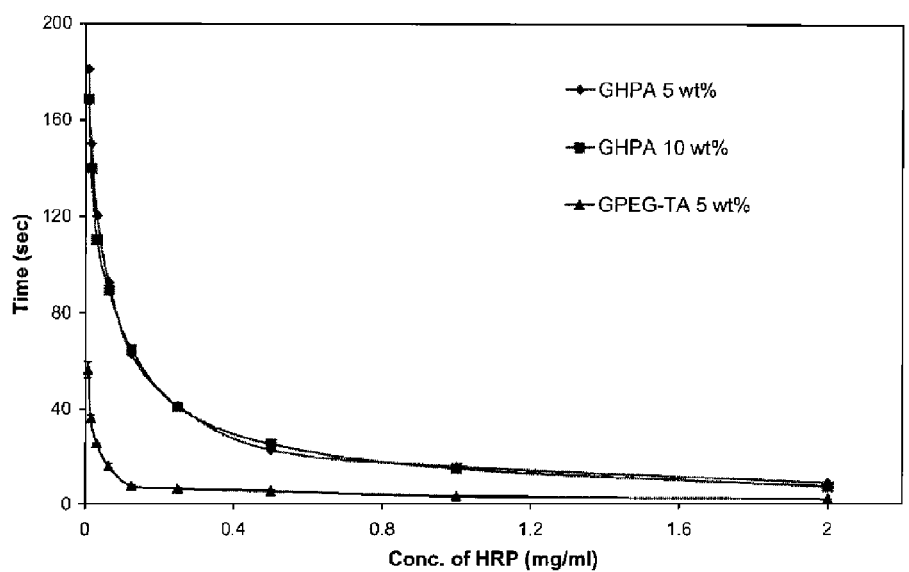
FIG. 17 is a graph showing the gelation time of GPEG-TA and GHPA hydrogels with enzyme concentrations.

The gelation time was found to be controlled within the range of from 5 to 180 sec depending on the concentration of HRP, as shown in FIG. 17. The gelation time decreased with increasing HRP concentration because an increase in the concentration of HRP promotes the degradation of $H_2O_2$ into radicals which mediate the formation of gel.

In addition, at the same HRP concentrations, GPEG-TA hydrogel exhibited a short gelation time compared to GHPA hydrogel, indicating that because the GPEG-TA polymer with PEG introduced between the polymer backbone (gelatin) and the tyramine moiety is greater in reactivity than is GHPA with the phenol moiety directly bonded to the polymer backbone (gelatin), more effective tyramine-tyramine bonds could be formed.

EXPERIMENTAL EXAMPLE 12

Comparison of Mechanical Strength between GPEG-TA and GHPA Hydrogel and Changes in the Mechanical Strength of GPEG-TA with $H_2O_2$ Concentration Using a rheometer, GPEG-TA hydrogel was evaluated for mechanical strength depending on hydrogen peroxide concentration. The hydrogel used had a final concentration of 5 wt %.

Figure 18:
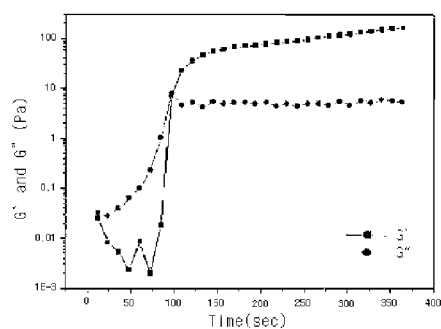
FIG. 18 is a set of graphs showing the mechanical strengths of GPEG-TA and GHPA hydrogels and the mechanical strength of GPEG-TA hydrogel varying with $H_2O_2$ levels.
Figure 18:
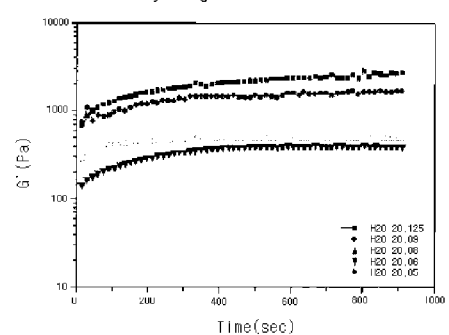

Under the same conditions (HRP, hydrogel peroxide level, polymer level), GHPA hydrogel and GPEG-TA hydrogel were observed to have mechanical strengths of 100 Pa and 2700 Pa, respectively (see FIG. 18). This can be explained by the fact that compared to GHPA with the phenol moiety directly bonded to the polymer backbone, GPEG-TA with PEG introduced between the polymer backbone and the tyramine moiety exhibits greater reactivity and thus a higher degree of crosslinking.

Depending on the concentration of hydrogen peroxide, the hydrogel ranged in mechanical strength from 90 to 2700 Pa.

Therefore, as shown in FIG. 18, GPEG-TA with PEG serving as a linker is superior in mechanical strength to GHPA and the in situ forming hydrogel can be provided with various mechanical strengths by controlling the concentration of hydrogel peroxide.

TABLE 1

| Polymer Solution | HRP (mg/ml) | $H_2O_2$ (wt %) | G' (Pa) |
|---|---|---|---|
| GHPA 5 wt % | 0.125 | 0.125 | 100 |
| GPEG-TA 5 wt % | | 0.125 | 2700 |
| | | 0.09 | 1700 |
| | | 0.08 | 500 |
| | | 0.06 | 400 |
| | | 0.05 | 90 |

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A composition of enzyme-triggered in situ-forming injectable hydrogel, represented by the following Chemical Formula 2, comprising:

two or more homogeneous or heterogeneous polymers, represented by the following Chemical Formula 1, bonding to each other by a dehydrogenation reaction between phenol or aniline moieties on adjacent polymers, wherein a polymer backbone is grafted with one of the phenol or aniline moieties by a linker, wherein the polymers are in situ crosslinked in vivo in the presence of horseradish peroxidase and hydrogen peroxide to form the hydrogel,

[Chemical Formula 1]

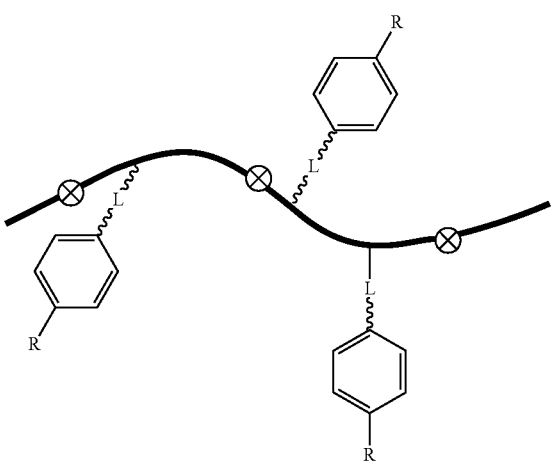

[Chemical Formula 2]

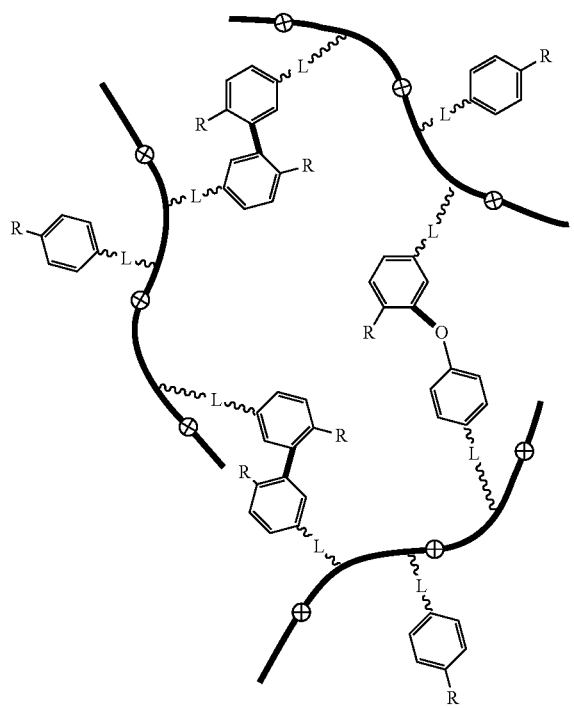

wherein,

R is hydroxyl or amine, and

L is selected from the group consisting of polyethyleneglycol (PEG), polyethylene oxide (PEO), polyethylenimine (PEI), polypropylene oxide (PPO), polyvinyl alcohol (PVA), poly(N-isopropylacrylamide) (polyNIPAAM), polyfumarate, polyorganophosphazene, polyacrylic acid (polyAAc), polyacrylsulfonate, poly hydroxyethylmethacrylate(PolyHEMA), and copolymers thereof.

2. The composition according to claim 1, wherein the polymer of Chemical Formula 1 is prepared by grafting a phenol or aniline derivative represented by the following Chemical Formula 3 to a polymer backbone having amino, hydroxyl or carboxyl groups by an amide, urethane, urea or ester bond, with a water-soluble polymer serving as a linker:

[Chemical Formula 3]

wherein, $R^1$ is a hydroxyl group or an amine group; and $R^2$ is a carboxyl group or an amine group.

3. The composition according to claim 1, wherein the polymer backbone is selected from the group consisting of gelatin, chitosan, heparin, cellulose, dextran, dextran sulfate, chondroitin sulfate, keratan sulfate, dermatan sulfate, alginate, collagen, albumin, fibronectin, laminin, elastin, vitronectin, hyaluronic acid, fibrinogen, a multi-arm polymer and a combination thereof.

4. The in situ forming injectable hydrogel composition according to claim 1, wherein the phenol is selected from the group consisting of tyramine, hydroxyphenylacetic acid, hydroxyphenylpropionic acid, and a combination thereof.

\* \* \* \* \*